US00PP23030P3

(12) United States Plant Patent
Bartel

(10) Patent No.: US PP23,030 P3
(45) Date of Patent: Sep. 11, 2012

(54) **VARIETY OF *CHAMAESYCE* PLANT NAMED 'SUMMER SNOW'**

(50) Latin Name: ***Chamaesyce hypericifolia* (Euphorbiaceae)/*Euphorbia hypericifolia***
Varietal Denomination: SUMMER SNOW

(75) Inventor: Dietmar Bartel, Eufurt (DE)

(73) Assignee: Sibylle Eich, Grolsheim (DE)

( * ) Notice: Subject to any disclaimer, the term of this patent is extended or adjusted under 35 U.S.C. 154(b) by 0 days.

(21) Appl. No.: 12/928,415

(22) Filed: Dec. 10, 2010

(65) Prior Publication Data

US 2012/0151647 P1 Jun. 14, 2012

(51) Int. Cl.
*A01H 5/00* (2006.01)

(52) U.S. Cl. ..... Plt./302

(58) Field of Classification Search ..... Plt./302
See application file for complete search history.

*Primary Examiner* — Annette Para
(74) *Attorney, Agent, or Firm* — The Webb Law Firm

(57) ABSTRACT

A new and distinct *chamaesyce* plant is provided which exhibits a compound, round habit and large flower bracts with small leaves.

3 Drawing Sheets

Botanical classification: *Chamaesyce hypericifolia* (Euphorbiaceae)/*Euphorbia hypericifolia.*
Varietal denomination: 'SUMMER SNOW'.

BACKGROUND OF THE INVENTION

The present invention comprises a new and distinct cultivar of *chamaesyce* botanically classified as *Chamaesyce hypericifolia* (Euphorbiaceae)/*Euphorbia hypericifolia* and known by the varietal name 'SUMMER SNOW'. The new variety was discovered in an open planting area in the summer of 2008 in Erfurt, Germany as a naturally occurring mutation of 'DIAMOND FROST' (unpatented). Subsequently, the new variety was asexually reproduced by vegetative cuttings in Erfurt, Germany in September of 2008. Erfurt, Germany is a mountainous area in Central Europe with a very dry climate.

The following characteristics distinguish the new variety from *chamaesyce* varieties known to the breeder:

Compact and round habit;
More homogeneous;
Small leaves with big flower bracts; and
Unique asexual reproduction.

Further, 'SUMMER SNOW' has a much more compact growth habit than 'DIAMOND FROST'.

The new variety has been trial and field tested and has been found to retain its distinctive characteristics and remain true to type through successive asexual propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
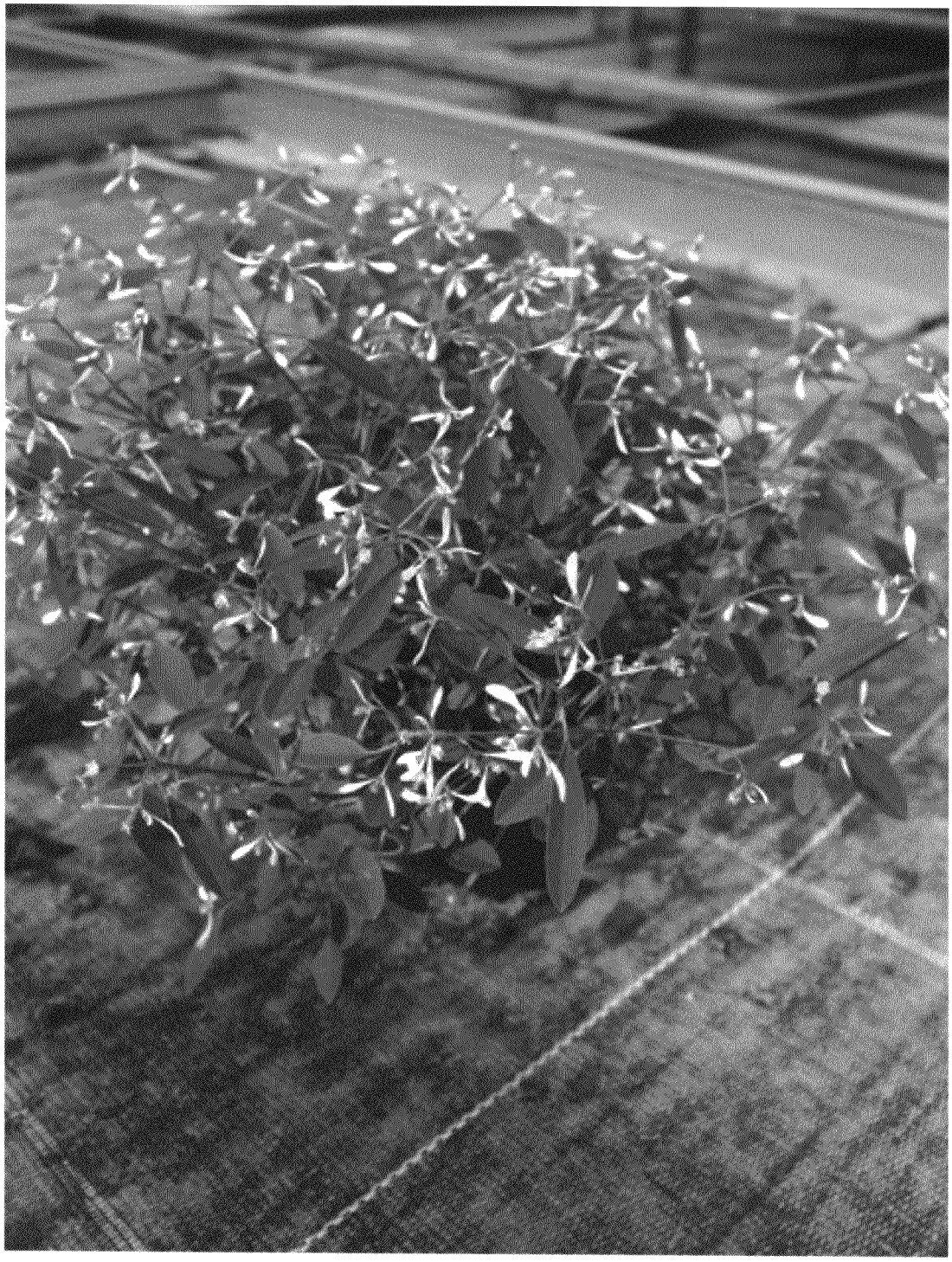
FIG. 1 is a photograph of an entire plant of the new variety.
Figure 2:
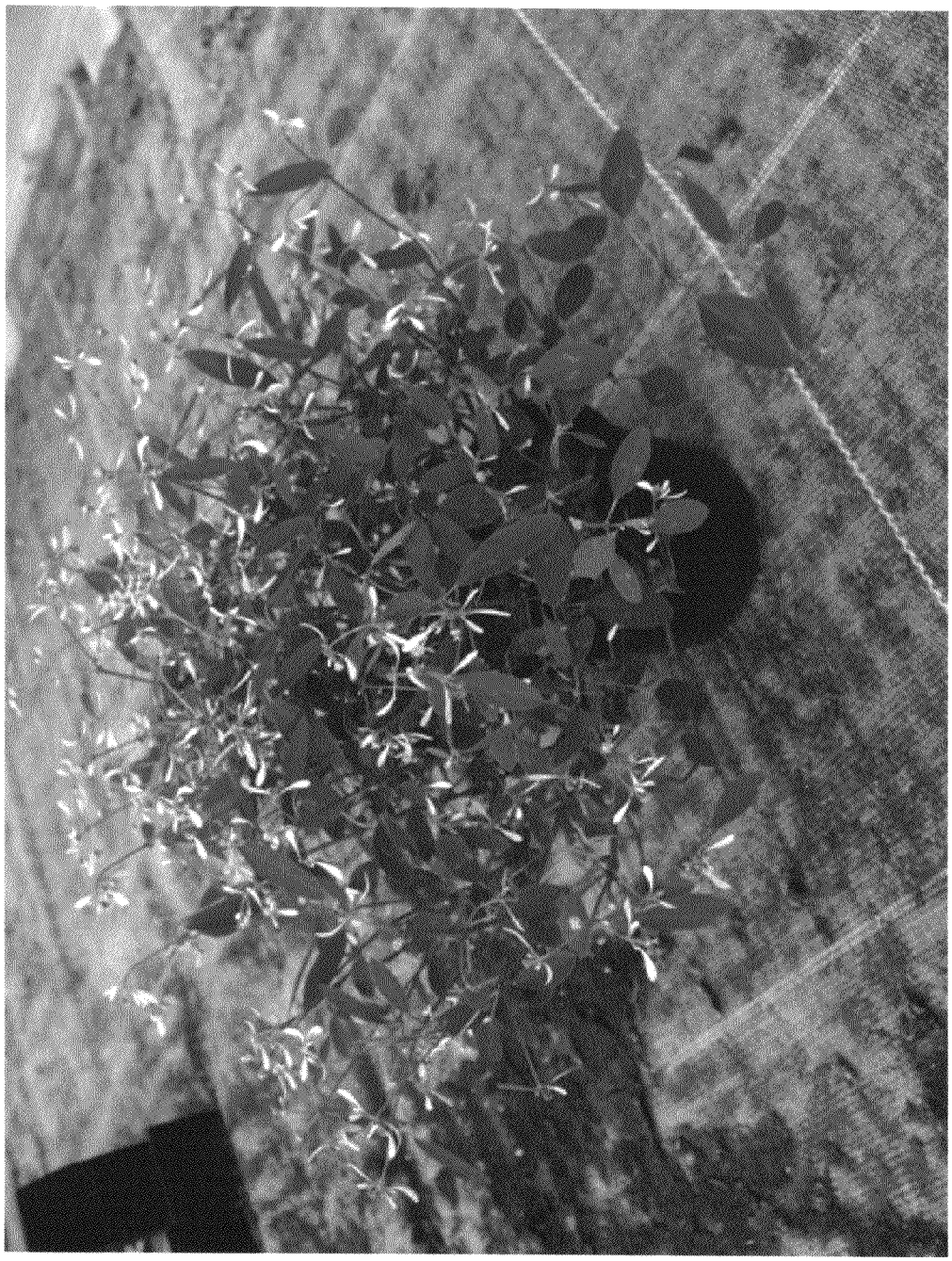
FIG. 2 is a photograph of an entire plant of the new variety.
Figure 3:
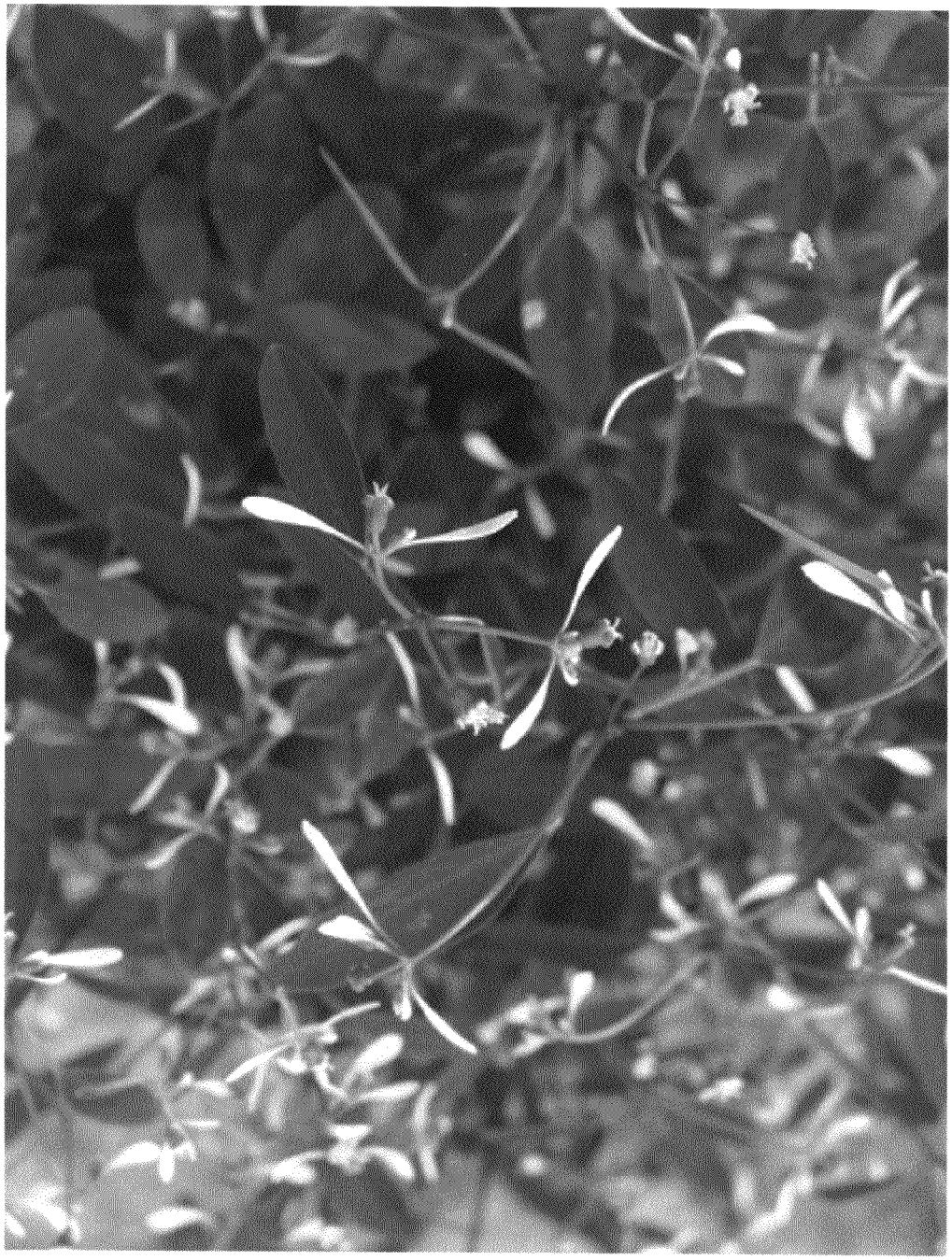
FIG. 3 is a close-up photograph of the flowers and leaves of the new variety.

The following detailed description sets forth the characteristics of the new cultivar. The new variety was grown in a glass-covered greenhouse in Grolsheim, Germany with shade during the summer and no shade starting in September. Growing temperatures ranged from 12-28° C. The new variety was 4 months old from planting in an 11 cm. pot by itself when described. Color references are primarily to The R.H.S. Colour Chart of The Royal Horticultural Society of London and were identified under natural light.

PLANT

Time to initiate roots: 10 days at an average temperature of 20° C.
Time to develop roots: 15 days at an average temperature of 20° C.
Rooting habit: Fibrous with a prop root system.
Plant form: Round and branching; moderate growing; cymose inflorescences.
Height (from soil to top of foliage): 30 cm.
Plant diameter: 30 cm.
Branching habit: Upright and freely branching.
Main stem:
- *Form.*—Round.
- *Color.*—RHS 146A.
- *Texture.*—Plain, succulent, and glabrous.
- *Length.*—5-10 cm.
- *Diameter.*—2-3 cm.
- *Internode length.*—5-7 cm.

Lateral branches:
- *Number.*—3-5 cm.
- *Color.*—RHS 146A.
- *Texture.*—Plain, succulent, and glabrous.
- *Length.*—5-7 cm.
- *Diameter.*—1 cm.
- *Internode length.*—3-5 cm.

Foliage:
- *Arrangement.*—Panicle.
- *Number of leaves per branch.*—10.
- *Size of leaf.*—Length: 4 cm. Width: 1.5 cm.
- *Shape of leaf.*—Oval to elliptical.
- *Apex shape.*—Acute to obtuse.
- *Base shape.*—Acute to obtuse.

*Margin*.—Entire.
*Texture*.—Hairy, pilose, and pubescent.
*Color*.—Young leaves: Upper surface: RHS 146A. Lower surface: RHS 146B. Mature leaves: Upper surface: RHS 147A. Lower surface: RHS 147B.
*Petiole*.—Length: 2.5 cm. Diameter: 0.5-1 mm. Color: RHS 146A.
*Veins*.—Venation type: Pinnate. Upper and lower surface color: RHS 147C.

FLOWER

Natural flowering season: Continuous flowering from spring to autumn in Central Europe.
Flower type and habit: Single rotate flowers arranged in umbel-like terminal cymes. Flowers are persistent and not fragrant.
Number of flowers per plant: 300-500.
Bud (described in a closed state, 1 day before opening):
*Shape*.—Urceolate.
*Diameter*.—1-1.5 mm.
*Length*.—1.5-2.5 mm.
*Color*.—RHS 146A at the base with white spots on the top.
Flower:
*Shape*.—Cathia is urceolate.
*Diameter*.—2-2.5 mm.
*Length*.—3-5 mm.
*Bract*.—Length: 9-10 mm. Width: 3-4.5 mm. Number: 1-3 per flower.
*Apex shape*.—Oblanceolate to obtuse.
*Texture*.—Plain and glabrous.
*Color*.—When opening: Upper surface: RHS 155C. Lower surface: RHS 155D. Fully opened: Upper surface: RHS 155C. Lower surface: RHS 155D.
Sepal:
*Number*.—5.
*Length*.—1-2 mm.
*Width*.—0.2-0.4 mm.
*Shape*.—Round.
*Apex shape*.—Rounded to apex.
*Base shape*.—Entire.
*Margin*.—Entire.
*Color*.—RHS 155D.
Peduncle:
*Length*.—5-6 cm.
*Diameter*.—0.5-1 mm.
*Color*.—RHS 146B.

REPRODUCTIVE ORGANS

Stamens:
*Number*.—3-4 per cyathia.
*Filament length*.—0.5-1 mm.
*Anthers*.—Shape: Oval. Length: 0.2-0.5 mm. Color: RHS 158C.
*Pollen*.—Color: RHS 158D. Amount: Scarce.
Pistils:
*Length*.—3 mm.
*Style*.—Length: 0.1-0.3 mm. Color: RHS 155D.
*Ovaries*.—Length: 0.1-0.2 mm. Color: RHS 146A.
*Stigma*.—Shape: 5 parted. Color: RHS 155D.

GENERAL

Disease resistance: Very high resistance to powdery mildew and common insects.
Weather tolerance: The new variety grows between 10-40° C. It tolerates heavy rain periods and very dry periods without stopping flowering.
Lasting quality: Flowers generally last between 10-18 days, but last longer in moderate climate conditions.
Seed/fruit production: None observed to date.

I claim:

1. A new and distinct variety of *chamaesyce* plant substantially as is herein described and illustrated.

* * * * *